United States Patent [19]

Adams

[11] Patent Number: 5,039,436

[45] Date of Patent: Aug. 13, 1991

[54] COUPLED POLYAMINE LUBRICANT ADDITIVES DERIVED FROM HYDROCARBYL POLYNITRILES AND POLYAMINES

[75] Inventor: Paul E. Adams, Willoughby Hills, Ohio

[73] Assignee: The Lubrizol Corporation, Wickliffe, Ohio

[21] Appl. No.: 606,296

[22] Filed: Oct. 31, 1990

Related U.S. Application Data

[62] Division of Ser. No. 400,651, Aug. 30, 1989, Pat. No. 4,976,881, which is a division of Ser. No. 853,575, Apr. 18, 1986, Pat. No. 4,906,392.

[51] Int. Cl.$^5$ ............................................. C10M 133/46
[52] U.S. Cl. ................................ 252/47; 252/51.5 A; 252/52 R
[58] Field of Search ........................ 252/47, 51.5 A, 52

[56] References Cited

U.S. PATENT DOCUMENTS

| | | | |
|---|---|---|---|
| 2,194,419 | 3/1940 | Chwala | 544/296 |
| 2,245,129 | 6/1941 | Greenwalt | 260/404.5 |
| 2,468,163 | 4/1949 | Blair et al. | 252/8.55 |
| 2,878,234 | 3/1959 | Peterson | 548/353 |
| 3,347,645 | 10/1967 | Pretsch et al. | 44/63 |
| 3,415,750 | 12/1968 | Anzenberger | 252/51.5 |
| 4,104,179 | 8/1978 | Colclough | 252/32.7 |
| 4,234,435 | 11/1980 | Meinhardt et al. | 252/51.5 R |
| 4,446,037 | 5/1984 | Horodysky et al. | 252/47.5 |
| 4,536,311 | 8/1985 | Horodysky et al. | 252/51.5 R |
| 4,976,881 | 12/1990 | Adams | 252/47 |

FOREIGN PATENT DOCUMENTS 0886968 5/1981 Belgium .
2755687 8/1978 Fed. Rep. of Germany .

OTHER PUBLICATIONS

P. L. de Benneville et al., "Nitrile Groups. IV. The Catalyzed Reaction of Nitriles with Amines in Water", *Journal of Organic Chemistry*, vol. 21, No. 10, Oct. 29, 1956, pp. 1072-1076.

*Heterocyclic Chemistry, The Pyrimidines;* Supplement I, D. J. Brown, John Wiley & Sons, New York, 1970, p. 52.

A. Marxer, "The Acylation and Alkylation of Imidazolines and Some News Types of Imidazolines", *Journal of the American Chemical Society*, vol. 79, No. 2, Jan. 29, 1957, pp. 467-472.

*Primary Examiner*—Jacqueline V. Howard
*Attorney, Agent, or Firm*—Robert A. Franks; Frederick D. Hunter; Forrest L. Collins

[57] ABSTRACT

Coupled polyamine additives for lubricants, fuels and functional fluids have been discovered. The coupled polyamines are prepared by the cyclization reaction of at least one reactant polyamine reactant with at least one hydrocarbyl polynitrile. This coupled polyamine may be further reacted with a hydrocarbyl carboxylic acid or derivative thereof, a hydrocarbyl phenolic reactant or mixtures thereof to provide an additive having greater oil solubility as well as imparting dispersancy and VI improvement.

9 Claims, No Drawings

COUPLED POLYAMINE LUBRICANT ADDITIVES DERIVED FROM HYDROCARBYL POLYNITRILES AND POLYAMINES

CROSS REFERENCE TO RELATED APPLICATIONS

This application is a division of Ser. No. 400,651 filed on Aug. 30, 1989, now U.S. Pat. No. 853,575 filed on Apr. 18, 1986, now U.S. Pat. No. 4,906,392.

BACKGROUND OF THE INVENTION

1. Field of the Invention

This invention relates to coupled polyamine additives for functional fluids and lubricant compositions, e.g., crankcase oils, automatic transmission fluids (ATF's), hydraulic fluids as well as fuel compositions. The novel coupled polyamine additives of the present invention are derived from a polyamine and a polynitrile reactant which generally form at least one cyclic reaction product. This reaction product may be further reacted with a carboxylic acylating agent or a phenolic reactant to form higher molecular weight products having greater solubility in various functional fluids and lubricants as well as imparting dispersancy and VI improvement.

2. State of the Art

Coupled amine reaction products, particularly heterocyclic nitrogen-containing reaction products are known and have been disclosed in the related patent and technical literature. For example, U.S. Pat. No. 2,468,163 discloses various imidazoline compounds which are useful for preventing corrosion of various metals. The imidazoline compounds of this patent are prepared from a polyamine and a carboxylic acid.

In U.S. Pat. No. 2,505,247, a process for the preparation of imidazolines is disclosed. The process of this invention reacts a diamine with a mononitrile compound in the presence of hydrogen sulfide to give the desired imidazoline compounds which are found to be useful as therapeutic agents.

U.S. Pat. No. 3,415,750 discloses polyalkenylsuccinimido imidazolines and polyalkenylsuccinimido bis-imidazolines which find utility as ashless dispersants in lubricating oil compositions. The imidazolines of this patent are derived from a polyethylene polyamine and a carboxylic acid.

In U.S. Pat. No. 3,347,645, a multi-purpose gasoline additive package is disclosed. The active component of the additive package is an alkenylsuccinic anhydride reaction product with an imidazoline or piperizine reactant. It is disclosed that the imidazoline or piperizine reactants are derived from polyamines, and a carboxylic acid.

It is disclosed in U.S. Pat. No. 4,104,179 that azoleamino polysulfides or azineamino polysulfides may be derived from an imidazole or imidazoline reactant and which compounds confer good anti-wear and good antioxidant properties on lubricating oils or fuel oils.

In U.S. Pat. No. 4,446,037, a reaction product of a hydrolized imidazoline, a mercaptan and an aldehyde and this reaction product further reacted with a boron compound which is useful as a friction reducing additive for lubricant composition is disclosed.

U.S. Pat. No. 4,536,311 discloses hydroxyalkyl hydrocarbyl imidazoline-acyl sarcosine reaction products which exhibit good friction reducing and anti-rust properties when used in lubricant compositions and fuel compositions.

U.S. Pat. No. 4,234,435 discloses novel carboxylic acid acylating agents and the derivatives thereof which are useful as lubricant additives. It is disclosed in this patent that various polyamines including cyclic heteronitrogen amine reactants may be reacted with the carboxylic acid acylating agent to form higher molecular weight dispersant and lubricant additive products.

In Marxer, *J.A.C.S.*, 79, 467 (1957) and In De Benneville et al., *J.O.C.*, 21, 1072 (1956), it is disclosed that various heterocyclic nitrogen compounds may be prepared from polyamines and various mononitriles.

None of the foregoing disclosures teach coupled polyamines derived from polynitrile and polyamine reactants nor that such reaction products may be further reacted with a carboxylic acid acylating reactant or phenolic type reactant.

SUMMARY OF THE INVENTION

In accordance with the present invention, a novel class of coupled polyamines derived from polynitrile reactants and polyamine has been discovered.

Further, in accordance with the invention, the novel coupled polyamines may be further reacted with hydrocarbyl carboxylic acid acylating agents or hydrocarbyl phenolic reactants to form higher molecular weight products which are useful to impart viscosity index (VI) improvement and dispersancy for functional fluids.

Still further, in accordance with the present invention, it has been found that the coupled polyamines of the invention may be used alone as additives for functional fluids, e.g., lubricant and fuel compositions, or may further be reacted with, for example, hydrocarbyl acylating agents to give higher molecular weight additive products.

Still further, in accordance with the invention, various functional fluids, including lubricating oils, automatic transmission fluids (ATF), hydraulic fluids as well as fuel compositions, comprising the coupled polyamines of the invention or their reaction products with an acylating agent or a phenolic reactant are contemplated and are within the scope of the invention.

These and other aspects of the invention will become clear to those skilled in the art upon the reading and understanding of the specification.

DETAILED DESCRIPTION OF THE INVENTION

A novel, class of coupled polyamines has been discovered and is illustrated by the following formula:

$$\left[ \begin{array}{c} \diagup N \diagdown \\ -(CHR^1)_n \phantom{xx} C- \\ \diagdown N \diagup \\ | \\ R^3 \end{array} R^2 \right]_u \quad (I)$$

wherein n is 2–7; $R^2$ is hydrocarbyl; $R^1$ is the same or different for each methylene carbon atom and is hydrogen, alkyl, $(Y-NR^4)_xR^5$, wherein x is 1 to about 100, Y is alkylene of 1 to about 7 carbon atoms, a heterocyclic nitrogen containing cycloalkylene of 1 to about 10 carbon atoms, $R^4$ is hydrogen, alkyl or $NH_2R^6[NR^7R^6]_y$ wherein $R^6$ is an alkylene group of 1 to about 10 carbon atoms, $R^7$ is independently H, alkyl or $R^6$ and y ranges from 1 to about 6, $R^5$ is hydrogen, hydrocarbyl or (I); $R^3$ is hydrogen, alkyl or (I); and u is 2 to about 6.

As used herein the terms "hydrocarbyl" or "hydrocarbon-based" denote a radical having a carbon atom directly attached to the remainder of the molecule and having predominantly hydrocarbon character within the context of this invention. Such radicals include the following:

(1) Hydrocarbon radicals; that is, aliphatic, e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, any two indicated substituents may together form an alicyclic radical). Such radicals are known to those skilled in the art; examples are (2) Substituted hydrocarbon radicals; that is, radicals containing non-hydrocarbon substituents which, in the context of this invention, do not alter the predominantly hydrocarbon character of the radical. Those skilled in the art will be aware of suitable substituents; examples are (3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

Terms such as "alkyl-based radical", "aryl-based radical" and the like have meaning analogous to the above with respect to alkyl and aryl radicals and the like.

The radicals are usually hydrocarbon and especially lower hydrocarbon, the word "lower" denoting radicals containing up to seven carbon atoms. They are preferably lower alkyl or aryl radicals, most often alkyl.

The cyclic reaction products, i.e., the coupled polyamines of the present invention, are derived from at least one hydrocarbyl polynitrile and at least one polyamine wherein each of these reactants is capable of undergoing a cyclization reaction to form a heterocyclic nitrogen containing product. An advantageous feature of the present invention is that this reaction may be conducted in one step by heating the reactants at a relatively low temperature in the presence or absence of a catalyst. While the catalyst is not particularly critical to the present invention, if a catalyst is utilized, hydrogen sulfide is the most preferred catalyst.

It is an advantageous feature of the present invention that the reaction may be conducted by heating at a temperature of less than 150° C. The temperature may range from about 70° C. up to about 200° C. Preferably, the temperature for the reaction will range from about 90° C. to about 150° C. As a most preferred range, the temperature will vary from about 110° C. to about 130° C.

With respect to the reactants utilized to prepare the cyclic reaction products of the present invention, the only criticality is that the polyamine reactant contain at least 2 amine groups, one of which must be a primary and the other may be primary or secondary, spacially arranged such that the desired heterocyclic reaction product may be formed. The polynitrile reactant must contain at least 2 nitrile, i.e., cyano, groups such that each of these reactants are capable of undergoing cyclization to give a heterocyclic nitrogen- containing product. It is preferred that the reacting amine groups are from 1,2 to 1,5 with respect to their relative positions on the carbon chain. It is most preferable that the amine groups are 1,2 or 1,3 as to their relative positions on the carbon chain.

The polyamine reactants useful within the scope of the present invention may be represented by the following formula:

wherein $R^5$ is independently hydrogen or hydrocarbyl; $R^4$ is hydrogen, alkyl or $NH_2R^6[NR^7R^6]_y$ wherein $R^6$ is alkylene of 1 to about 10 carbon atoms, $R^7$ is H or alkyl or $R^6$, y ranges from 1 to about 6; Z is alkylene of 1 to about 10 carbon atoms; and p ranges from 1 to about 100; with the proviso that said polyamine comprises at least two reacting amine groups which are positioned with respect to each other such that they are capable of undergoing a cyclization reaction with a polynitrile reactant.

A preferred group of polyamines as defined by formula (II) above is where said polyamine contains at least 2 amino groups positioned on the carbon chain such that they are capable of undergoing a cyclization reaction with a polynitrile reactant and where the alkylene group contains 2 to about 7 carbon atoms.

The amine reactants of the present invention may contain aliphatic, cycloaliphatic or aromatic groups and may contain unsaturated sites in the molecule. These amines may also contain non-hydrocarbon substituents or groups as long as these groups do not significantly interfere with the reaction of the amines with the hydrocarbyl polynitrile reactants of the invention. Such non-hydrocarbon substituents or groups include lower alkoxy, lower alkyl mercapto, nitro, and interrupting groups such as $-CH_2CH_2-X-CH_2CH_2-$ where X is $-O-$, $-S-$ or $-P-$.

Higher molecular weight hydrocarbyl polyamines may be used as the polyamine coupling agent. These polyamines are generally prepared by reacting a chlorinated polyolefin having a molecular weight of at least about 400 with ammonia or the appropriate amine. Such amines are known in the art and described, for example, in U.S. Pat. Nos. 3,275,554 and 3,438,757, both of which are expressly incorporated herein by reference for their disclosure in regard to how to prepare these amines.

Another group of amines suitable for use as amine reactant (II) are branched polyalkylene polyamines. The branched polyalkylene polyamines are polyalkylene polyamines wherein the branched group is a side chain containing on the average at least one nitrogen-bonded aminoalkylene group.

These polyamines may be expressed by the formula:

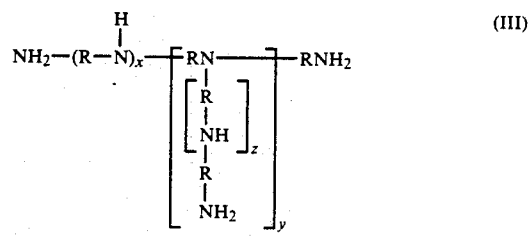

wherein R is an alkylene group such as ethylene, propylene, butylene and other homologues (both straight chained and branched), etc., but preferably ethylene; and x, y and z are integers, x being for example, from 4 to 24 or more but preferably 6 to 18, y being for example 1 to 6 or more but preferably 0 to 1. The x and y units may be sequential, alternative, orderly or randomly distributed.

A preferred class of such polyamine reactants includes those of the formula:

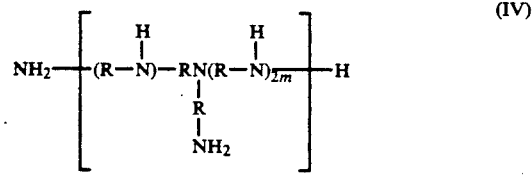

(IV)

wherein m is an integer, for example, 1–20 or more but preferably 1–3, wherein R is preferably ethylene, but may be propylene, butylene, etc. (straight chained or branched).

U.S. Pat. Nos. 3,200,106 and 3,259,578 are expressly incorporated herein by reference for their disclosure of how to make such polyamines.

Another preferred class of amine reactants for use in the present invention is alkylene polyamines, including the polyalkylene polyamines, which are described in more detail hereafter. The alkylene polyamines include those conforming t the formula:

(V)

wherein q is from 1 to about 10; each $R''$ is independently a hydrogen atom, a hydrocarbyl group or a hydroxysubstituted hydrocarbyl group having up to about 30 atoms, and the "Alkylene" group has from 1 to about 10 carbon atoms, but the preferred alkylene is ethylene or propylene. Especially preferred are the alkylene polyamines where each $R''$ is hydrogen with the ethylene polyamines and mixtures of ethylene polyamines being the most preferred. Usually q will have an average value of from about 2 to about 7. Such alkylene polyamines include methylene polyamines, ethylene polyamines, butylene polyamines, propylene polyamines, pentylene polyamines, hexylene polyamines, heptylene polyamines, etc. The higher homologs of such amines and related aminoalkyl-substituted piperazines are also included.

The alkylene polyamines used for the purposes of the present invention, must, as pointed out above, contain at least two (2) reacting amine groups which are positioned with relationship to each other such that the polyamine is capable of undergoing a cyclization reaction with a polynitrile reactant.

Alkylene polyamines useful in preparing the compositions of the present invention include ethylene diamine, triethylene tetramine, propylene diamine, trimethylene diamine, hexamethylene diamine, di(hexamethylene)triamine, tripropylene tetramine, tetraethylene pentamine, trimethylene diamine, pentaethylene hexamine, di(trimethylene)triamine, and the like. Higher homologs, as are obtained by condensing two or more of the above-illustrated alkylene amines, are useful as the polyamine reactant as are mixtures of two or more of any of the aforedescribed polyamines.

Ethylene polyamines, such as those mentioned above, are especially useful for reasons of cost and effectiveness. Such polyamines are described in detail under the heading "Diamines and Higher Amines" in *The Encyclopedia of Chemical Technology*, Second Edition, Kirk and Othmer, Volume 7, pages 27, 39, Interscience Publishers, Division of John Wiley and Sons, 1965, which is hereby incorporated by reference for its disclosure of useful polyamines.

Other useful types of polyamine reactant mixtures are those resulting from stripping of the above-described polyamine mixtures. In this instance, lower molecular weight polyamines and volatile components are removed from an alkylene polyamine mixture to leave as residue what is often termed "polyamine bottoms." In general, alkylene polyamine bottoms can be characterized as having less than two, usually less than 1% by weight material boiling below about 200° C. In the instance of ethylene polyamine bottoms, which are readily available and found to be quite useful, the bottoms contain less than about 2% by weight total diethylene triamine (DETA) or triethylene tetramine (TETA). A typical sample of such ethylene polyamine bottoms obtained from the Dow Chemical Company of Freeport, Texas designated "E-100" showed a specific gravity at 15.6° C. of 1.0168, a percent nitrogen by weight of 33.15 and a viscosity at 40° C. of 121 centistokes. Gas chromatography analysis of such a sample showed it to contain about 0.93% "Light Ends" (DETA), 0.72% TETA, 21.74% tetraethylene pentamine and 76.61% pentaethylene hexamine and higher (by weight). These alkylene polyamine bottoms include cyclic condensation products such as piperazine and higher analogs of diethylene triamine, triethylene tetramine and the like. Another source of such polyamine bottoms is "Polyamine HPA" which can be obtained from Union Carbide Corp.

With regard to the polynitrile reactants, these reactants, like the polyamine reactants, require only that the reactant contain at least two cyano groups and are capable of undergoing a cyclization reaction with the polyamine reactant. These reactants may be represented by the following formula:

(VI)

wherein $R'''$ is hydrocarbyl and a is 2–6.

The polynitrile reactants of the present invention may contain aliphatic, cycloaliphatic, aromatic, or heterocyclic, including aliphatic-substituted aromatic, aliphatic-substituted heterocyclic, cycliphatic substituted aliphatic, cycloaliphatic-substituted aromatic, cycloaliphatic-substituted heterocyclic, aromatic-substituted aliphatic, aromatic-substituted cycloaliphatic, aromatic-substituted heterocyclic, hetero-cyclic-substituted aliphatic, heterocyclic-substituted alicyclic, and heterocyclic-substituted aromatic groups and may contain unsaturated sites in the molecule. The polynitriles may also contain non-hydrocarbon substituents or groups as long as these groups do not interfere with the cyclization reaction with the amine reactants of the invention. Such non-hydrocarbon substituents or groups include lower alkoxy, lower alkyl mercapto, nitro, interrupting groups such as —O—, —S—, —N— and —P— (e.g., as in such groups as —CH$_2$CH$_2$—X—CH$_2$CH$_2$— where X is —O—; —S—; —N—; or —P—.

According to one embodiment of the invention, one class of polynitrile reactants as defined by the above formula (VI), is where the hydrocarbyl group R''' is ethylene, propylene, butylene, (methylene)$_a$X, (ethylene)$_a$X or (propylene)$_a$X where a is 2 or 3 and X is O, N, P or S. A preferred class of polynitrile reactants is where the hydrocarbyl group is (methylene)$_2$X, (ethylene)$_2$X or (propylene)$_2$X, where X is O or S.

Examples of suitable polynitrile reactants according to the present invention include adiponitrile, alpha-methyleneglutaronitrile, 3,3'-iminodipropionitrile, 1,3,6-tricyanohexane and the like. Various representative hetero atom containing polynitrile reactants include nitrilotrisethaneamine, bis-2-cyanoethyl-ether and bis-2-cyanoethylthioether and the like. There may also be mentioned various cyanoethylated nitro compounds of the formula:

(VII)

wherein x is 2 or 3, R' or R is CH$_3$, H O. Also, there may be mentioned various cyanoethylated carbonyl compounds of the formula:

(VIII)

wherein R is H or hydrocarbyl, x is 2 or 3; if x is 2, R' is H or C$_{1-20}$ alkyl.

Additionally, there may be mentioned various cyclic polynitrile compounds, for example, 2,2,6,6-tetracyanoethyl or tetracyanopropylcyclhexanone.

As previously discussed, the reaction of the above two reactants is a one-step process conducted in the presence or absence of a catalyst and by heating. The relative amount of the reactant is not particularly critical and will be controlled by the stoichiometry and economics of the reaction. Thus, for example, the reaction of adiponitrile with tetraethylenepentamine may be in a 1:1 molar ratio or in any other possible variation thereof. The controlling factor will be the economics as well as the desired end product. Thus, as will be recognized by the chemist of ordinary skill, there is no preferred amount for each reactant in carrying out the cyclization reaction where this will be controlled by such extraneous factors as cost, necessary reaction temperatures and the like.

The preparation of various coupled polyamines within the scope of the present invention is illustrated in the following examples. While these examples will show one skilled in the art how to operate within the scope of this invention, they are not to serve as a limitation on the scope of the invention where such scope is defined only in the claims. It is pointed out that in the following examples common elsewhere in the present specification and claims, all percentages and all parts are intended to express percent by weight and parts by weight unless otherwise clearly indicated.

EXAMPLE I

A mixture of 1500 parts (34.6 equivalents) of commercial ethylene polyamine bottoms, 404 parts (5.77 equivalents) of bis-2-cyanoethyl thioether, and 4 parts of gaseous hydrogen sulfide is heated at 110° to 115° C. for 3 hours under a nitrogen atmosphere. The product is a mixture which contains 27.7% nitrogen and 4.31% sulfur.

EXAMPLE II

A mixture of 600 parts (13.86 equivalents) of commercial ethylene polyamine bottoms, 243 parts (3.47 equivalents) of bis-2-cyanoethyl thioether, and 2 parts of gaseous hydrogen sulfide is heated at 125° C. for 1 hour under a nitrogen atmosphere. The product is a mixture which contains 26.5% nitrogen and 6.73% sulfur.

EXAMPLE III

A mixture of 400 parts (9.24 equivalents) of commercial ethylene polyamine bottoms, 98 parts (1.85 equivalents) of commercial a-methyleneglutaronitrile, and 2 parts of gaseous hydrogen sulfide is heated at 120° to 125° C. for 6 hours under a nitrogen atmosphere. The product is a mixture which contains 27.5% nitrogen (27.7% theory).

EXAMPLE IV

A mixture of 286 parts (7.11 equivalents) of commercial ethylene polyamine bottoms containing 50% by weight diethylene tetramine, 100 parts (1.43 equivalents) of bis-2-cyanoethyl thioether, and 1 part of gaseous hydrogen sulfide is heated at 115° to 120° C. for 4 hours under a nitrogen atmosphere. The product is a mixture which contains 27.7% nitrogen and 5.23% sulfur.

EXAMPLE V

A mixture of 250 parts (6.22 equivalents) of commercial ethylene polyamine bottoms containing 50% by weight diethylene tetramine, 96.4 parts (1.24 equivalents) of 2,2,6,6-tetracyanoethyl cyclohexanone, and 2 parts of gaseous hydrogen sulfide is heated under a nitrogen atmosphere at 120° to 125° C. for 5 hours. The product is a mixture which contains 26.3% nitrogen (26.5% theory).

While the cyclic reaction products or coupled polyamines of the present invention may be useful by themselves as additives for lubricants, they may be further reacted to form even higher molecular weight products to improve their oil solubility and further impart dispersancy and/or greater VI improvement. For the purposes of this invention, a substance is considered to substantially improve the viscosity properties of a composition if its incorporation in the composition in operative amounts causes an increase in its viscosity index (as determined by ASTM procedure D2270) of at least 6 units.

In general, materials which may be used to further react with the coupled polyamine products of the present invention are reagents and reactants which are described in the patent and technical literature. Among the materials that may be utilized for the purposes of the present invention to further react with the above-described coupled polyamine products to form a higher molecular weight material, there is first mentioned various hydrocarbyl carboxylic acid acylating reagents. The carboxylic acids suitable for use in this invention include aliphatic, cycloaliphatic, and aromatic mono- and polybasic carboxylic acids such as the naphthenic acids, alkyl- or alkenyl-substituted cyclopentanoic acids, alkyl-or alkenyl-substituted cyclohexanoic acids, alkyl- or alkenyl-substituted aromatic carboxylic acids. The aliphatic acids generally contain at least eight carbon atoms and preferably at least twelve carbon atoms. Usually, they have no more than about 400 carbon atoms. Generally, if the aliphatic carbon chain is branched, the acids are more oil-soluble for any given carbon atoms content. The cycloaliphatic and aliphatic carboxylic acids can be saturated or unsaturated. Specific examples include 2-ethylhexanoic acid, linolenic acid, propylene-tetramer-substituted succinic acid, behenic acid, isostearic acid, pelargonic acid, capric acid, palmitoleic acid, linoleic acid, lauric acid, oleic acid, ricinoleic acid, undecyclic acid, dioctylcyclopentane carboxylic acid, myristic acid, dilauryldecahydronaphthalene carboxylic acid, stearyloctahydroindene carboxylic acid, palmitic acid, commercially available mixtures of two or more carboxylic acids such as tall oil acids, rosin acids and the like.

A preferred group of oil-soluble carboxylic acids useful in preparing the compositions of the present invention are the oil-soluble aromatic carboxylic acids. These acids are represented by the general formula:

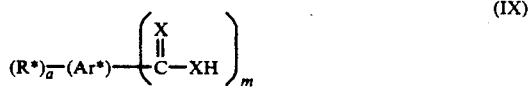

(IX)

where R* is an aliphatic hydrocarbon-based group of at least four carbon atoms, and no more than about 400 aliphatic carbon atoms, a is an integer of from one to four, Ar* is a polyvalent aromatic hydrocarbon nucleus of up to about 14 carbon atoms, each X is independently a sulfur or oxygen atoms, and m is an integer of from one to four with the proviso that R* and a are such that there is an average of at least 8 aliphatic carbon atoms provided by the R* groups for each acid molecule represented by Formula (IX). Examples of aromatic nuclei represented by the variable Ar* are the polyvalent aromatic radicals derived from benzene, naphthalene, anthracene, phenanthrene, indene, fluorene, biphenyl, and the like. Generally, the radical represented by Ar* will be a polyvalent nucleus derived from benzene or naphthalene such as phenylenes and naphthylene, e.g., methylphenylenes, ethoxyphenylenes, nitrophenylenes, isopropylphenylenes, hydroxyphenylenes, mercaptophenylenes, N,N-diethylaminophenylenes, chlorophenylenes, dipropoxynaphthylenes, triethylnaphthylenes, and similar tri-, tetra-, penta- valent nuclei thereof, etc.

The R* groups are usually purely hydrocarbyl groups, preferably groups such as alkyl or alkenyl radicals. However, the R* groups can contain small number substituents such as phenyl, cycloalkyl (e.g., cyclohexyl, cyclopentyl, etc.) and non-hydrocarbon groups such as nitro, amino, halo (e.g., chloro, bromo, etc.), lower alkoxy, lower alkyl mercapto, oxo substituents (i.e., =O), thio groups (i.e., =S), interrupting groups such as —NH—, —O—, —S— and the like provided the essentially hydrocarbon character of the R* group is retained.

Examples of R* groups include butyl, isobutyl, pentyl, octyl, nonyl, dodecyl, docosyl, tetracontyl, 5-chlorohexyl, 4-ethyoxypentyl, 4-hexenyl, 3-cyclohexyloctyl, 4-(p-chloro-phenyl)-octyl, 2,3,5-trimethylheptyl, 4-ethyl-5-methyloctyl, and substituents derived from polymerized olefins such as polychloroprenes, polyethylenes, polypropylenes, polyisobutylenes, ethylene-propylene copolymers, chlorinated olefin polymers, oxidized ethylene-propylene copolymers and the like. Likewise, the group Ar* may contain non-hydrocarbon substituents, for example, such diverse substituents as lower alkoxy, lower alkyl mercapto, nitro, halo, alkyl or alkenyl groups of less than four carbon atoms, hydroxy, mercapto and the like.

A group of particularly useful carboxylic acids are those of the formula:

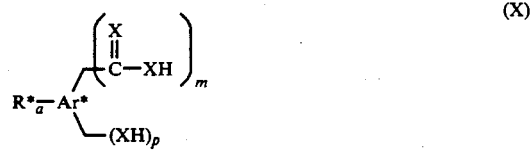

(X)

where R*, X, Ar*, m and a are defined in Formula (IX) and p is an integer of 1 to 4, usually 1 or 2. Within this group, an especially preferred class of oil-soluble carboxylic acids are those of the formula:

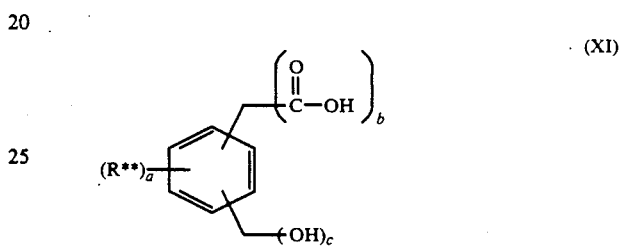

(XI)

where R is an aliphatic hydrocarbon group containing at least 4 to about 400 carbon atoms, a is an integer of from 1 to 3, b is 1 or 2, c is zero, 1, or 2 and preferably 1 with the proviso that R and a are such that the acid molecules contain at least an average of about twelve aliphatic carbon atoms in the aliphatic hydrocarbon substituents per acid molecule. And within this latter group of carboxylic acids, the aliphatic hydrocarbon substituted salicylic acids wherein each aliphatic hydrocarbon substituent contains an average of at least about sixteen carbon atoms per substituent and one to three substituents per molecule are particularly useful. Salts prepared from such salicylic acids wherein the aliphatic hydrocarbon substituents are derived from polymerized olefins, particularly polymerized lower 1-mono-olefins such as polyethylene, polypropylene, polyisobutylene, ethylenepropylene copolymers and the like and having average carbon contents of about 30 to about 400 carbon atoms.

The carboxylic acids corresponding to Formulas (IX)-(XI) above are well known or can be prepared according to procedures known in the art. Carboxylic acids of the type illustrated by the above formula and processes for preparing their neutral and basic metal salts are well known and disclosed, for example, in such U.S. Pat. Nos. as 2,197,832; 2,197,835; 2,252,662; 2,252,664; 2,174,092; 3,410,798 and 3,595,791.

Another type of carboxylic acid reactant used in this invention are those from alkenyl succinic acids, the anhydrides and derivatives thereof having the general formula:

(XII)

wherein R* is as defined above in Formula (IX). Such acids and means for making them are set forth in U.S.

Pat. No. 3,271,130; 3,567,637 and 3,632,510, which are hereby incorporated by reference in this regard.

A preferred class of alkenyl succinic acids are substituted succinic acids or derivatives thereof consisting of substituent groups and succinic groups wherein the substitution groups are derived from polyalkylenes, which is characterized by a Mn value of 500 to about 10,000 and a Mw/Mn value of 1.0 to about 4.0.

Phenolic reactants are also useful in the compositions of this invention and are well known to those skilled in the art. The phenolic reactants are of the general formula:

  (XIII)

wherein $R^*$, n, $Ar^*$, X and m have the same meaning and preferences as described hereinabove with reference to Formula (IX). The same examples described with respect to Formula (IX) also apply. When the phenolic reactant does not include a carboxylic group, another coupling agent, such as an aldehyde or ketone, may be required.

A commonly available class of phenolic reactants are those phenols of the general formula:

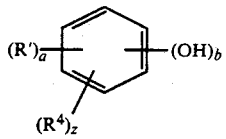  (XIV)

wherein a is an integer of 1–3, b is 1 or 2, z is 0 or 1, R' is a substantially saturated hydrocarbon-based substituent having an average of from 30 to about 400 aliphatic carbon atoms and $R^4$ is selected from the group consisting of lower alkyl, lower alkoxyl, nitro and halo groups.

Other phenolic reactants that are useful are those that are made from phenols that have been linked through alkylene (e.g., methylene) bridges. These are made by reacting single or multi-ring phenols with aldehydes (e.g., formaldehyde) or ketones, typically, in the presence of an acid or basic catalyst. Such linked phenates as well as sulfurized phenols are described in detail in U.S. Pat. No. 3,350,038; particularly columns 6–8 thereof, which is hereby incorporated by reference for its disclosures in this regard.

Naturally, mixtures of two or more of the hereinabove described carboxylic acids and phenols can be used in the compositions of this invention, including mixtures of two or more of any of these.

The foregoing additives/dispersants are generally prepared in the same manner as the coupled polyamines of the present invention. In other words, they are prepared by the reaction of at least one of the coupled polyamines of the present invention with at least one of the reactive materials described hereinabove at an elevated temperature, preferably in the range of 100° C. to about 250° C. and most preferably in the range of about 150° C. to about 200° C.

The following examples are provided to illustrate various additives/dispersants prepared or derived from reaction of the coupled polyamine materials of the present invention with such other reactant materials as described above. Again, it is emphasized that these examples are provided for illustrative purposes only and are not to serve as a limitation on the scope of the invention where such scope is set out solely in the claims.

EXAMPLE A

A mixture of 1600 parts (2.82 equivalents) of polyisobutenyl succinic anhydride, 369 parts (6.49 equivalents) of the coupled polyamine prepared in Example II, and 1413 parts of diluent oil was heated at 165° C. for 12 hours under a nitrogen atmosphere. A total of 17 parts of by-product water had collected in a Dean-Stark trap. The hot mixture was filtered through a filter aid to obtain the desired product. The product contains 2.73% nitrogen (2.70% theory).

EXAMPLE B

A mixture of 1464 parts (2.64 equivalents) of polyisobutenyl succinic anhydride, 161 parts (3.19 equivalents) of the coupled polyamine prepared in Example I, and 1140 parts of diluent oil was heated at 170° to 175° C. for 16 hours under a nitrogen atmosphere. A total of 14 parts of by-product water had collected in a Dean-Stark trap. The mixture was filtered through a filter aid at 150° to 155° C. to obtain the desired product. The product contains 1.64% nitrogen (1.62% theory).

EXAMPLE C

To a mixture of 648 parts (1.02 equivalents) of polyisobutenyl succinic anhydride and 800 parts of diluent oil under a nitrogen atmosphere at 165° C., was added 64 parts (1.27 equivalents) of the coupled polyamine prepared in Example IV over a 2 hour period. The mixture was heated at 175° to 180° C. for 10 hours. A total of 8 parts of by-product water had been collected in a Dean-Stark trap. The hot mixture was filtered through a filter aid to obtain the desired product. The product contains 1.21% nitrogen (1.18% theory) and 0.19% sulfur (0.22% theory).

EXAMPLE D

A mixture of 1400 parts (2.47 equivalents) of polyisobutenyl succinic anhydride, 180.8 parts (3.40 equivalents) of the coupled polyamine prepared in Example V and 1050 parts of diluent oil was heated under a nitrogen atmosphere at 185° to 190° C. for 12 hours. A total of 16 parts of by-product water had been collected in a Dean-Stark trap. The mixture was filtered at 155° to 160° C. through a filter aid to obtain the desired product. The product contains 1.89% nitrogen (1.90% theory).

EXAMPLE E

A mixture of 1200 parts (1.10 equivalents) of polyisobutenyl phenol, 72.6 parts (2.20 equivalents) of paraformaldehyde, and 58.1 parts (1.10 equivalents) of the coupled polyamine prepared in Example II is heated under a nitrogen atmosphere at 165° C. for 10 hours. The by-product water is collected in a Dean-Stark trap, and the hot mixture is filtered through a filter aid to obtain the derived product.

The compositions according to the present invention, which specific species have been illustrated in the above Examples I–V and A–E, are versatile additives for lubricating compositions and fuels as well as functional fluids. The compositions of the present invention are useful additives for imparting VI improvement as well as enhancing dispersancy, detergency, antioxidant properties and anti-wear properties of various lubricant compositions. The compositions or additives of the present invention may also find use in functional fluids including fuel compositions, automatic transmission fluids, hydraulic fluids and the like.

The composition of the present invention may be formulated with a functional fluid by the direct blending of the composition to the particular functional fluid, e.g., lubricating oil, or it may be formulated with the functional fluid in the form of a concentrate. Such a concentrate may be prepared by adding 1% to about 99% by weight of the composition or additive of the present invention to a substantially inert, normally liquid organic diluent or solvent such as benzene, toluene, xylene, petroleum naphtha, mineral oil, ethyleneglycol monomethyl ether or the like.

The compositions of the present invention formulated with the particular functional fluid or concentrate may contain other additives and chemistries such as dispersants, anti-oxidants, and the like. Such other additives and chemistries include, for example, detergents and dispersants of the ash-producing or ashless type, corrosion- and oxidation-inhibiting agents, pour point depressing agents, extreme pressure agents, color stabilizers, anti-foam agents and VI improvers. These other additives and chemistries are fully described and disclosed in U.S. Pat. No. 3,541,014; U.S. Pat. No. 4,289,635; and U.S. Pat. No. 4,266,945 which disclosures of these patents relating to such other additives and chemistries are hereby incorporated by reference for such disclosures.

To further illustrate various functional fluid compositions, specifically lubricant compositions, comprising the compositions of the present invention, the following illustrative examples are provided. It is again pointed out that the following examples are provided for illustrative purposes only and are not to place any limitation on the scope of the invention where such scope is set out only in the claims. All parts and percentages are by weight.

Table I sets out the results from testing the additives of the present invention in the standard Ford V-D test as well as the standard CAT 1H-2 and CAT 1G-2 test.

TABLE I

| EXAMPLE NO. | RESULTS[1] OF V-D | RESULTS[2] OF CAT 1H-2(H) OR CAT 1G-2(G) |
|---|---|---|
| C | 6.94[3] | 5/182 (H)[3] |
| A | 7.58[4] | 54/311 (G)[5] |
| D | none | 35/382 (G)[6] |
| B | none | 52/189 (G)[7] |

[1] average engine varnish
[2] top groove filling/weighted total demerits based on coverage and location of deposits
[3] run at 2.8% weight of the additive of Example C in a fully formulated package in a mineral oil[8]
[4] run at 4.2% weight of the additive of Example A in a fully formulated package in a mineral oil[8]
[5] run at 6.3% weight of the additive of Example A in a fully formulated package in a mineral oil[8]
[6] run at 5% weight of the additive of Example D in a fully formulated package in a mineral oil[8]
[7] run at 6.5% weight of the additive of Example B in a fully formulated package in a mineral oil[8]
[8] the fully formulated package contains a detergent, an antioxidant, an EP/antiwear agent, a corrosion inhibitor and VI improver.

While the invention has been described and illustrated with reference to certain preferred embodiments thereof, those skilled in the art will appreciate that various changes, modifications and substitutions can be made therein without departing from the spirit of the invention. For example, different concentration ranges other than the preferred ranges set forth hereinabove may be applicable as a consequence of variations in the oil base stock or the type of engine or the like. It is intended, therefore, that the invention be limited only by the scope of the claims which follow.

What is claimed is:

1. A composition comprising a major amount of an oil of lubricating viscosity and a minor amount of an additive prepared by reacting:

(A) at least one reactant of the formula:

$$\left\{ -(CHR^1)_n-C\diagup^{\diagdown N}_{\diagdown N-R^3}-R^2 \right\}_u \quad (I)$$

wherein n is 2–7; $R^2$ is hydrocarbyl; $R^3$ and each $R^1$ independently are hydrogen, alkyl, $(Y-NR^4)_xR^5$, wherein x is 1 to about 100, Y is alkylene of 1 to about 7 carbon atoms or a heterocyclic nitrogen containing cycloalkylene of 2 to about 10 carbon atoms, $R^4$ is hydrogen, alkyl or $NH_2R^6[NR^7R^6[_y$ wherein $R^6$ is an alkylene group of 1 to about 10 carbon atoms, $R^7$ is independently H, alkyl or $R^6$ and y is 1 to about 6, $R^5$ is hydrogen or hydrocarbyl or (I); and u is 2 to about 6; with (B) at least one hydrocarbyl phenolic reactant.

2. The composition of claim 1, wherein (A) is derived from at least on hydrocarbyl dinitrile selected from the group consisting of cyanomethylthioether, cyanoethylthioether or cyanopropylthioether; and a polyamine selected from the group consisting of triethylenetetramine, diethylenetriamine, tetraethylenepentamine, pentaethylenehexamine, polyamine bottoms and mixtures thereof.

3. The composition of claim 1, wherein $R^2$ is $(CH_2)_aS-(CH_2)_bCN$, where a and b are independently 1 to 5, n is 2 and $R^1$ is $-(YNR^4)_xR^5$, where x is 5 or 6 and Y is ethylene or propylene, $R^4$ and $R^5$ are both H and $R^2$ on the other carbon atom is H and n is 2.

4. The composition of claim 1 wherein $R^2$ is $-(CH_2)_2-S-CH_2)_2$ and u is 2.

5. The composition of claim 1, wherein n is 2.

6. The composition of claim 1, wherein (B) has the formula:

$$(R^*)_a-(Ar^*)-(XH)_m$$

wherein $R^*$ is an aliphatic hydrocarbon-based group having 4 to about 400 aliphatic carbon atoms, a is an integer of 1 to 4, $Ar^*$ is a polyvalent aromatic hydrocarbon nucleus having up to about 14 carbon atoms, each X is independently a sulfur or oxygen atom, and m is an integer of 1 to 4.

7. The composition of claim 1, wherein (B) has the formula:

[benzene ring with substituents $(OH)_b$, $(R')_a$, $(R^4)_z$]

wherein a is an integer of 1 to 3, b is 1 or 2, z is 0 or 1, R' is a substantially saturated hydrocarbon-based substituent having an average of 30 to about 400 aliphatic carbon atoms, and $R^4$ is lower alkyl, lower alkoxyl, nitro or halo.

8. The composition of claim 1, wherein (B) is a linked phenate, prepared by reacting one or more phenols with an aldehyde or ketone.

9. The composition of claim 1, wherein (B) is a sulfurized phenol.

* * * * *